(12) United States Patent
Holland et al.

(10) Patent No.: US 7,550,283 B2
(45) Date of Patent: Jun. 23, 2009

(54) **BACTERIOPHAGE FOR LYSIS OF *METHYLOBACTERIUM* AND COMPOSITIONS AND USES THEREOF**

(75) Inventors: Mark A. Holland, Salisbury, MD (US); Nicole Lenihan, Owings Mills, MD (US)

(73) Assignee: Salisbury University, Salisbury, MD (US)

( * ) Notice: Subject to any disclaimer, the term of this patent is extended or adjusted under 35 U.S.C. 154(b) by 630 days.

(21) Appl. No.: 10/821,640

(22) Filed: Apr. 9, 2004

(65) Prior Publication Data

US 2005/0136037 A1   Jun. 23, 2005

Related U.S. Application Data

(60) Provisional application No. 60/461,874, filed on Apr. 10, 2003.

(51) Int. Cl.
*C12N 7/00* (2006.01)
(52) U.S. Cl. .................................................. 435/235.1
(58) Field of Classification Search ............... 435/235.1
See application file for complete search history.

(56) References Cited

U.S. PATENT DOCUMENTS

| 5,268,171 | A  | 12/1993 | Polacco et al. |
|-----------|----|---------|----------------|
| 5,512,069 | A  | 4/1996  | Holland et al. |
| 5,961,687 | A  | 10/1999 | Joshi et al.   |
| 6,174,837 | B1 | 1/2001  | Joshi et al.   |
| 6,255,467 | B1 | 7/2001  | Lindner et al. |
| 6,329,320 | B1 | 12/2001 | Joshi et al.   |
| 2003/0032141 | A1 | 2/2003 | Nguyen et al. |

*Primary Examiner*—Bruce Campell
*Assistant Examiner*—Nicole Kinsey White
(74) *Attorney, Agent, or Firm*—Darlene A. Vanstone; Carolyn S. Elmore; Elmore Patent Law Group, P.C.

(57) ABSTRACT

The invention relates to a novel bacteriophage which is lytic for species of the genus *Methylobacterium*, Human Blood Bacterium (HBB) or both, and derivatives, progeny and recombinant and mutated forms thereof. The invention further relates to compositions, methods and kits for using the bacteriophage of the invention in agricultural and therapeutic settings.

5 Claims, 4 Drawing Sheets

BACTERIOPHAGE FOR LYSIS OF *METHYLOBACTERIUM* AND COMPOSITIONS AND USES THEREOF

RELATED APPLICATION

This application claims the benefit of U.S. Provisional Application No. 60/461,874 filed on Apr. 10, 2003. The entire teachings of the above application is incorporated herein by reference.

FIELD OF THE INVENTION

This invention relates to bacteriophage for lysis of bacteria of the genus *Methylobacterium*, Human Blood Bacterium (HBB), or both, and compositions and uses thereof.

BACKGROUND OF THE INVENTION

Bacteriophages (phages) are viruses that infect bacteria. Bacteriophage, which derive their name from the Greek word "phago" meaning "to eat" or "bacteria eaters", were independently discovered by Twort and by D'Herelle in the first part of the twentieth century. Early enthusiasm led to their use as both prophylaxis and therapy for diseases caused by bacteria. In the U.S. during the 1940's, Eli Lilly and Company (Indianapolis, Ind.) commercially manufactured six phage products for human use including preparations targeted towards *staphylococci, streptococci* and other respiratory pathogens. With the advent of antibiotics, the therapeutic use of phage gradually fell out of favor in the U.S. and Western Europe and little subsequent research was conducted. However, in the 1970's and 1980's there were reports of bacteriophage therapy continuing to be utilized in Eastern Europe, most notably in Poland and the former Soviet Union. In light of recent concerns that antibiotics are losing their effectiveness through overuse, there is renewed interest to the potential of phage therapy as a weapon against bacterial infection (Carlton, 1999. Arch. Immunol. Therap. Exper. 47:267-274; see also *News Focus, Science* (25 Oct. 2002) vol. 298).

Pink pigmented facultative methylotrophs (PPFMs) are bacteria in the genus *Methylobacterium*. PPFMs are ubiquitously distributed on plant surfaces, in soil containing organic matter and in water. They are not generally thought to be pathogenic, although recent reports indicate that the PPFMs might act as opportunistic pathogens in immuno-compromised patients. Previously, it has been demonstrated that PPFMs stimulate plant growth in vivo and in vitro, they participate in plant nitrogen metabolism (Holland and Polacco 1992. Plant Physiol.98:942-948), they enhance seed germination (Holland and Polacco 1994. Ann. Rev. Plant Physiol. Plant Molec. Biol. 45:197-209), they stimulate root growth (Holland 1997. Rec. Res. Dev. Plant Phys. 1:207-213) and they manufacture cytokinins (Holland et al. 2002, In: Lindow et al. (eds.) *Phyllosphere Microbiology*, APS Press, St. Paul, Minn.). These findings have led to the issuance of U.S. Pat. Nos. 6,329,320; 6,174,837; 5,961,687; 5,512,069 and 5,268,171. All of these patents are herein incorporated by reference. Other applications are pending directed to: 1) the isolation of elite strains of PPFMs found to provide increased yields of, for example, methionine and vitamin B12 in plants (see for instance U.S. patent application Ser. No. 09/958,175 filed May 8, 2002), and 2) for altering the fertility of a plant (U.S. patent application Ser. No 10/296,158). The entirety of these two applications is incorporated by reference herein.

Lindner et al., in U.S. Pat. No. 6,255,467, the entirety of which is incorporated by reference herein described the isolation of a bacterium from human blood, which he designated HBB (Human Blood Bacterium). Lindner et.al. represent that the bacterium is present in everyone's blood, but that high numbers of the bacterium are associated with the symptoms of auto-immune disorders including chronic fatigue syndrome, fibromyalgia, multiple sclerosis, lupus erythematosis and rheumatoid arthritis. The subject matter of the Lindner patent includes the use of the bacterium as a basis for diagnosing auto-immune disease and treatments for these disorders based on antibiotic therapy. Based on DNA sequencing of selected portions of the human blood bacterium genome, the bacterium was identified by Lindner et al. as a close relative of *Methylobacterium*.

The present inventors have identified and isolated the first known bacteriophage effective at infecting and lysing species of *Methylobacterium* (*Methylobacterium* spp.) from plant sources. In addition, it has now been found that this bacteriophage can selectively destroy the blood borne bacterium, HBB. No phages effective against *Methylobacterium* or HBB have been previously described in the literature.

SUMMARY OF THE INVENTION

In view of the foregoing, one embodiment of the invention relates to an isolated novel bacteriophage which is lytic for species of the genus *Methylobacterium*, HBB or both, and derivatives, progeny and recombinant and mutated forms thereof. In another embodiment, the invention relates to methods of eliminating *Methylobacterium* and particularly PPFM from the seeds, stems leaves, flowers and other parts of a plant comprising contacting the plant with an effective amount of the bacteriophage of the invention. In yet another embodiment, the invention relates to methods for producing male sterility in plants comprising contacting the plant with an effective amount of the bacteriophage of the invention. In another embodiment, the invention relates to methods of treating an infection by *Methylobacterium* or HBB in a patient comprising administering to the patient a therapeutically effective amount of a bacteriophage of the invention. In other embodiments, the invention relates to compositions and methods for treating autoimmune disease or opportunisitic infections in a patient comprising administering to the patient a therapeutically effective amount a bacteriophage of the invention. In yet another embodiment, the invention relates to compositions, methods and kits for disinfecting environmental surfaces that are contaminated with *Methylobacterium* comprising contacting the surface with an effective amount of the bacteriophage of the invention.

DETAILED DESCRIPTION OF THE INVENTION

Figure 1:
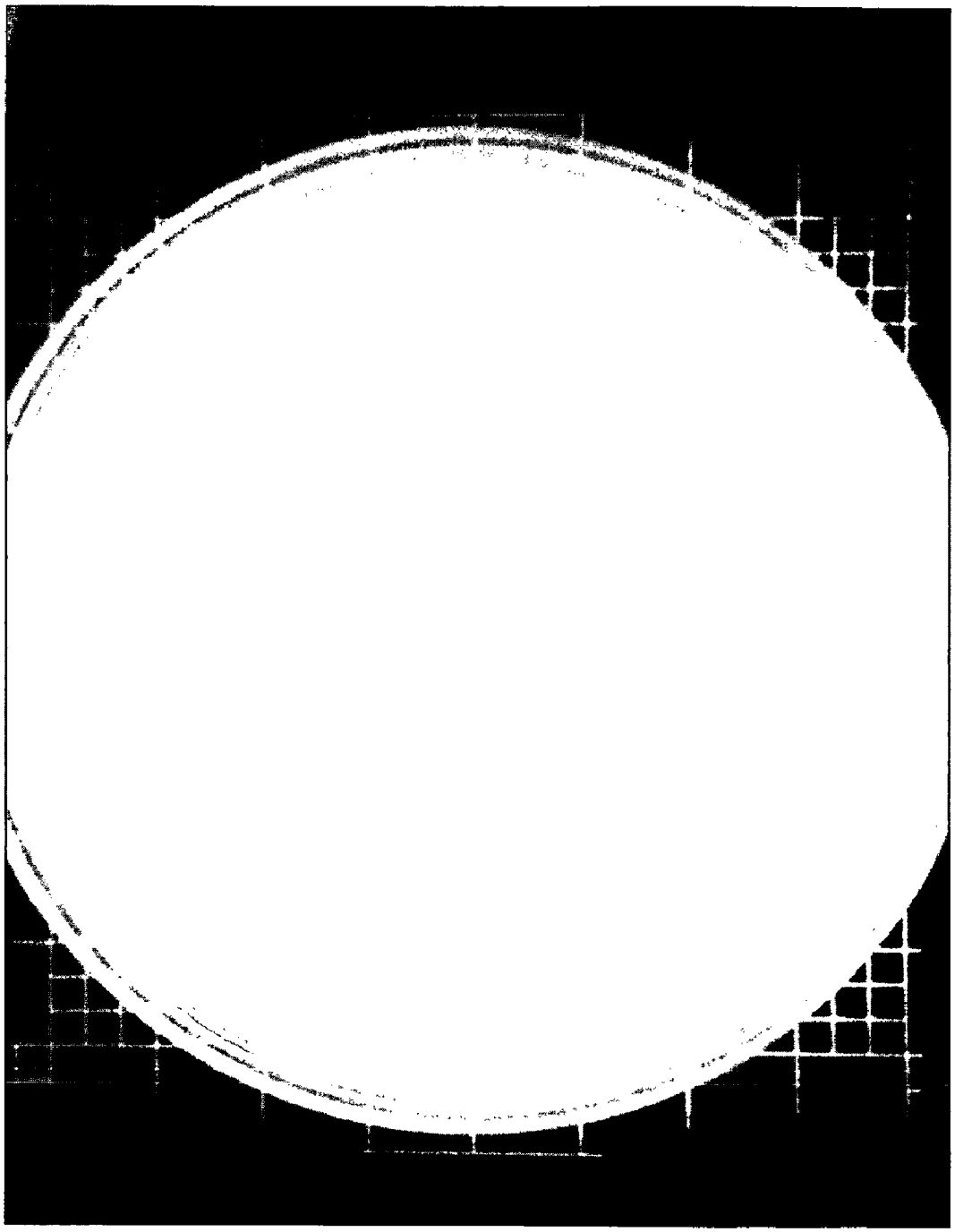
FIG. 1 is a micrograph showing phage-induced cell lysis of *Methylobacterium* isolated from a soybean plant.

A description of preferred embodiments of the invention follows.

The terms "bacteriophage" and "phage" are used interchangeably herein and broadly refer either to a single species of bacteriophage, or mixtures of species of bacteriophages, that are lytic for bacterial species of the genus *Methylobacterium*, HBB, or both. Preferred bacteriophage of the invention were deposited with the American Type Culture Collection (ATCC), located at Manassas, Va., USA, as ATCC# PTA-5075, on Mar. 21, 2003, under the terms of the Budapest Treaty on the International Recognition of the Deposit of Microorganisms for the Purposes of Patent Procedure and Regulations thereunder (Budapest Treaty), and is thus maintained and made available according to the terms of the Budapest Treaty. Availability of such bacteriophage is not to be construed as a license to practice the invention in contravention of the rights granted under the authority of any government in accordance with its patent laws.

The term "isolated bacteriophage" as used herein refers to a phage preparation that is at least enriched for bacteriophage virulent against *Methylobacterium* species, HBB, or both, and preferably further purified and detoxified in accordance with the methods known in the art and described herein.

The terms "treating" or "treatment" of a disease, condition or infection associated with HBB in a patient includes; prophylactic treatment of patients susceptible to disease, treatment at the initial onset of disease, treatment of ongoing disease, and treatment of relapsing disease in susceptible patients.

The term "therapeutically effective amount" as used herein means an amount of bacteriophage effective, at dosages and for periods of time necessary, to prevent, diminish, inhibit or eradicate symptoms of disease in a patient. A therapeutically effective amount of bacteriophage may vary according to factors such as the disease state, age, sex and weight of the individual. Dosage regimes may be adjusted to provide the optimum therapeutic response. For example, several divided doses may be administered daily or the dose may be proportionally reduced as indicated by the exigencies of the therapeutic situation.

The term "infection" by *Methylobacterium* or HBB as used herein refers to an amount of *Methylobacterium* or HBB that is above normal or desired amounts. For example, as discussed above, HBB is present in all "normal" persons, and therefore an "infection" by HBB as used herein refers to levels of HBB that are above those levels normally found in people. Therefore, the treatment of an HBB infection in a person means reducing the levels of HBB back to normal or back to desired amounts and not necessarily eradicating all HBB from the person.

In a first aspect, the invention provides an isolated bacteriophage that is lytic for species of the genus *Methylobacterium*, HBB or both. In one preferred embodiment, the bacteriophage is selected from the phage contained in ATCC# PTA-5075. In another preferred embodiment, the bacteriophage is selected from the progeny, derivatives and recombinant forms of the bacteriophage contained in ATCC # PTA-5075. Suitable bacteriophage of the invention may be isolated from any sample containing bacteriophage of the invention which are typically found in association with their host bacteria, (i.e. *Methylobacterium* species or HBB). Thus any source that might be expected to contain, for example, PPFM or HBB is suitable for use as a source of bacteriophage lytic for *Methylobacterium* or HBB. Such sources include but are not limited to, parts of plants such as leaves, seeds, stems and flowers that contain PPFM, or human blood samples or other human tissue or fluids that contain HBB.

In working with PPFM bacteria, the lab of the inventors found it difficult to remove native strains of the bacteria from plant material. The PPFMs resist being washed away, even with soaps, bleach and organic solvents like ethyl alcohol. The PPFMs are naturally resistant to many antibiotics. The best result achieved was to lower the populations of PPFMs resident on plants; however, the lab never eliminated them completely. For this reason, an attempt to isolate phages that would kill the PPFMs was made. Following classical microbiological methods, the lab succeeded in isolating such phages.

Thus in a second aspect of the invention, methods of isolating bacteriophages of the invention are provided comprising the steps of: a) obtaining bacteriophage from a sample that has been in contact with plant matter; b) plating the bacteriophage onto a medium comprising at least one *Methylobacterium* species derived from a plant or seeds of a plant; c) collecting plaques formed in the *Methylobacterium*-containing medium; d) purifying the isolated plaques. In one preferred embodiment, steps (b)-(d) are repeated with the product of step (d) until a virulent phage preparation is obtained.

In accordance with the invention, bacteriophages were isolated from water, soil, and plant material in the greenhouse attached to Devilbiss Hall on the Salisbury University Campus (Salisbury Md.) as follows: Water samples (with associated soil, plant material etc) from a floor drain, from around the base of flower pots, from the muck on the greenhouse benches, etc, were collected and returned to the lab. It was believed that since PPFM bacteria are native to these habitats, that viruses that infect them would be located in the same place. In the lab, 50 mL cultures of PPFM bacteria (soybean isolate, SL1, ATCC 202211) were inoculated with 1 mL aliquots of the greenhouse samples and incubated for 5 days on a shaker (225 rpm) at room temperature. This constituted an enrichment step, since it was expected that phages if present in the greenhouse samples, would be at very low titer. Following the enrichment, the cultures were centrifuged (7000 rpm, 10 minutes in a clinical, swinging bucket centrifuge) to remove whole cells and debris. Supernatants were then filtered through a 0.2 µm filter. Such a filter will allow bacteriophages to pass through, but will retain bacterial cells and cellular debris. The resulting phage suspensions were then streaked on lawns of *Methylobacterium* isolates to test their ability to lyse the bacteria. From these plates, individual phage plaques were selected for further testing and characterization. Standard methods for phage purification are described, for instance, in U.S. Pat. No. 6,121,036 the entirety of which is incorporated by reference herein. However, the citation of such methods is not to be considered restrictive or completely descriptive of the art.

Those skilled in the art are capable of obtaining an appropriate sample of the bacteriophage from a respective locus, now given the target or organism. Certainly, those skilled in the art are capable of growing bacteriophage in the bacterial host using conventional methods such as those described in, inter alia, Silhavy et al., *Experiments with Gene Fusion*, Cold Spring Harbor Laboratory, Cold Spring Harbor, N.Y. (1984) and Sambrook et al., *Moleculer Cloning: A Laboratory Manual*, 2nd Edition, Cold Spring Harbor, N.Y., pp. 2.73-2.81 (1989).

Phages are stored as cell lysates in the refrigerator (4° C.) with a drop of chloroform as a preservative. Alternatively, phages can be frozen or freeze-dried for storage. It is believed that under these conditions phage can be viably stored for years. Freeze-dried phages are stable essentially indefinitely.

Those skilled in the art are capable of selecting and separating the appropriate bacteriophage using the guidelines presented herein. Preferably, this mem, thod of growing the phage in a medium containing the bacteria, and then selecting, isolating and purifying phage from plaques is repeated a number of times until a virulent phage preparation is obtained.

The literature teaches that upon separating, or while growing in the medium together with the host or target organism, the bacteriophage also can be selected for virulence by subjecting it to various stringent conditions. For example, the phage preparation can be subjected to mutating conditions using a mutator host. Alternatively, the phage preparation medium can be subjected to irradiation by light and/or heat, it can be subjected to extreme variations in pH by addition of appropriate acid or caustic, the medium can be subjected to over-hydration or to drying conditions, extreme individual ionic concentration or heat shock. These various procedures are conducted on the phage medium to assure bacteriophage diversity and to increase the probability of selecting more virulent and more in vivo adaptable bacteriophages. Those bacteriophages that survive the aforementioned conditions then are separated using the methods described above, and purified. If desired, additional bacteriophage can be generated or cloned using techniques known to those skilled in the art, and the resulting preparations purified. Skilled artisans are capable of modifying, as necessary, the aforementioned testing methodology to select virulent phage preparations effective against *Methylobacterium*, HBB, or both, using the guidelines provided herein, and also are capable of separating and purifying the virulent phage preparations that survive any and/or all of the aforementioned testing protocol.

The bacteriophage samples that are the most virulent can be determined by plating on *Methylobacterium* or HBB using standard methods. The bacteriophage samples that are the most virulent then can be isolated, grown, purified and detoxified, if needed.

These purified bacteriophage preparations then can be administered to a test seed, whole plant, or test animal, all of which are normally colonized by *Methylobacterium* species or HBB. The virulence of the bacteriophage preparations can be determined by comparing the microbial counts of *Methylobacterium* or HBB from phage-treated organisms versus untreated controls. The bacteriophage preparations having the highest anti-bacterial activity can thus be selected. Preferably bacteriophage preparations capable of reducing bacterial load by at least 1 log and more preferably by at least 2 logs and even more preferably by at least 3 logs have suitable anti-bacterial activity for use in the methods of the invention.

The literature teaches that purified bacteriophage preparation can be subjected to ultrafiltration through a membrane or hollow fiber with a molecular weight cut-off of approximately $10^4$ to about $10^7$ daltons, preferably within the range of from about $10^5$ to about $10^6$ daltons. Alternatively, the phage preparations can be subjected to ultracentrifugation using preparations such as cesium chloride (i.e., at a concentration range of from about 60 to about 95 grams per mole), percoll, ficoll, (i.e., at about 50 to about 80%) or sucrose and glycerol (i.e., at about 5% to about 40%). Ultracentrifugation can be carried out at forces within the range of from about 50,000 Xg to about 90,000 Xg, preferably from about 60,000 Xg to about 80,000 Xg, for 2 or more hours for cesium chloride, sucrose and glycerol, or for example, from about 20,000 Xg to about 40,000 Xg, preferably from about 25,000 Xg to about 35,000 Xg for 20 to 30 minutes using percoll or ficoll.

The phage preparations can be detoxified by dialysis using the largest pore membrane that retains bacteriophages, where the membrane preferably has a molecular weight cut-off of approximately $10^4$ to about $10^7$ daltons, preferably within the range of from about $10^5$ to about $10^6$ daltons. Alternatively, the phage preparations can be detoxified using size exclusion chromatography using preparatory columns with an exclusion pore of any where from about $10^4$ to about $10^7$ daltons, preferably from about $10^5$ to about $10^6$ daltons.

Phage preparations which have been selected for-virulence then can be formulated into compositions that can be administered in large enough dosage and in adequate frequency to effect arrest or retardation of the growth of bacteria. Effective treatment regimens and dosages can be determined on a specific basis for different phage isolates and different hosts.

Thus, those skilled in the art will recognize that the effective amount for a seed, a plant, and mouse will differ from that of a man, and will differ according to the targeted species of *Methylobacterium* or HBB. The quantitative determinations can be readily determined by one of ordinary skill in the art.

In an alternative embodiment of the second aspect of the invention, methods for isolating bacteriophage lytic for HBB are provided comprising the steps of: a) obtaining bactieriophage from a human blood sample; b) plating the bacteriophage onto a medium comprising HBB; c) collecting plaques formed in the HBB-containing medium; and d) purifying the isolated plaques. In a preferred embodiment, steps (b)-(d) are repeated with the product of step (d) until a virulent phage preparation is obtained.

In a third aspect, the invention provides methods of removing *Methylobacterium* species from plants and seeds of plants comprising the step of contacting at least a portion of the plant or seed of a plant, with a bacteriophage which is lytic for a species of the genus *Methylobacterium* , in an amount sufficient to significantly reduce or eliminate the presence of *Metylobacterium* species on the plant, or seeds of the plant. In one embodiment, a reduction in bacterial load on the plant or seeds of the plant, by at least 1 log and preferably by at least 3 logs within 48-98 hours after phage administration as compared to a control, is considered significant. In one preferred embodiment, the bacteriophage is selected from the bacteriophage present in ATCC# PTA-5075. In another preferred embodiment, the *Methylobacterium* are selected from species of *Methylobacterium* that are native to the target plant being treated. In another preferred embodiment, the *Methylobacterium* is PPFM. In yet another preferred embodiment the PPFM are selected from the group consisting of *M. mesophilicum, M. organophilum* and *M. extorquens*.

Populations of PPFM bacteria resident on plant seeds and leaves are generally found to be $10^4$ to $10^6$ cfu per gram fresh weight. Accordingly, in another preferred embodiment, an effective amount of phage to significantly reduce or eradicate the presence of *Methylobacterium* spp on the plant, plant parts of seeds of the plant is in the range of about $10^4$ to $10^6$ pfu per mL, depending on the loss of phage or phage viability during application to the plant. Plants may be contacted with the phage by any number of means known in the art including spraying the plants with a phage formulation, or soaking the plant parts, particularly the seeds in a phage formulation.

Removal of *Methylobacterium* from the target plant, particularly native *Methylobacterium* spp. is desirable, for example, in the process of altering the metabolism of a plant as described in U.S. Pat. No. 5,268,171, incorporated herein by reference. Replacement of a native, symbiotic species of plant bacteria with genetically engineered bacterial species can alter plant enzyme activity and alter agronomic performance of a plant in a desired manner. It is often necessary to "cure" the plant, in whole or in part of the native bacterium prior to reintroducing genetically altered or engineered bacterial strains to alter agronomic activity of the plant in a desired manner. Applying mutant strains of PPFMS to the seeds of a plant is also described in U.S. Ser. No. 09/958,175.

In a fourth aspect, the invention provides methods for producing male sterility in plants, particularly flowering plants, comprising contacting at least a portion of the plant such as a leaf, stem, or flower, with a bacteriophage which is lytic for a species of the genus *Methylobacterium* in an amount that effects male sterility. The amount effective to sterilize a plant is generally that amount of bacteriophage that is necessary to significantly reduce or eliminate the presence of *Methylobacterium* spp. on the plant. In one embodiment, a reduction in bacterial load on the plant by at least 1 log and preferably by at least 3 logs within 48-98 hours after phage administration as compared to a control, is considered significant. In one preferred embodiment, the bacteriophage is selected from the bacteriophage present in ATCC# PTA-5075. In another preferred embodiment, the *Methylobacterium* are selected from species of *Methylobacterium* that are native to the target plant being treated. In another preferred embodiment, the *Methylobacterium* is PPFM. In yet another preferred embodiment the PPFM are selected from the group consisting of *M. mesophilicum, M. organophilum* and *M. extorquens*. Populations of PPFM bacteria resident on plant seeds and leaves are generally found to be $10^4$ to $10^6$ cfu per gram fresh weight. Accordingly, in another preferred embodiment, an amount of phage effective to sterilize a plant is in the range of about $10^4$ to $10^6$ pfu per mL, depending on the loss of phage or phage viability during application to the plant. Plants may be contacted with the phage by any number of means known in the art including spraying the plants with a phage formulation. Male-sterile plants in accordance with the invention are useful, for example, in the production of hybrid seeds as described in U.S. Pat. App. Publication No. 20030211082, incorporated herein by reference. Accordingly, in an alternative embodiment, a method for producing hybrid seeds is provided comprising the steps of (a) sterilizing a plant by contacting at least a portion of the plant with a bacteriophage which is lytic for species of the genus *Methylobacterium* in an amount effective to produce male sterility; (b) pollinating a flower from the male-sterile plant with pollen from a source of interest; and (c) collecting hybrid seeds from the plant.

As is demonstrated in U.S. Patent Application Publication No. 20030211082, Cytokinin under-producing strains of *Methylobacterium* were found to colonize cytoplasmic male sterile barley, and the low levels of cytokinin found in the plant are the reason for reduced fertility. To test this, *Methylobacterium* from both cytoplasmic male sterile and normal barley plants was isolated. Cytoplasmic male sterile barley was obtained from the National Plant Germplasm System—Small Grains Collection, at Aberdeen, Id. Wild type barley was obtained from a local seed merchant. PPFM isolates were obtained as previously described in Holland, M. A & Polacco, J. C. (1992) *Plant Physiol*. 98, 942-948, which is incorporated by reference herein in its entirety. Liquid cultures of the isolates were grown and 0.1 mL aliquots of the spent medium were assayed by Enzyme Linked Immunosorbent Assay (ELISA) for trans-Zeatin riboside content using a commercially available ELISA kit (Sigma Chemical Co., St. Louis, Mo.). In repeated experiments, the culture supernatant of PPFMs isolated from cytoplasmic male sterile barley contained only 10% as much trans-Zeatin riboside as that of the isolate from wild type barley (0.016 vs. 0.19 pmol/0.1 mL and 0.013 vs. 0.14 pmol/0.1 mL in two different experiments, for example).

Furthermore, U.S. Patent Application Publication No. 20030211082 showed cytokinin production (ng of trans-Zeatin riboside/liter of culture) by bacterial isolates from a) wild type barley, b) cytoplasmic male sterile barley (CMS), and c) CMS barley plants inoculated before planting with bacteria from the wild type plant (CMS+wild). Three separate determinations were made for a) and b) representing three separate experiments. Note that cytokinin production is routinely 10-fold higher in bacteria from wild type plants than in bacteria from CMS plants. Also, CMS plants inoculated with bacteria from wild type plants show restoration of fertility.

Therefore, replacement of a plant's normal bacterial population with cytokinin under-producers might be expected to produce male sterility. If indeed this is the case, then male sterility could be induced at will in any breeding line. Such a finding would be of enormous significance and utility to plant breeders.

Another treatment that could mimic inoculation with low cytokinin producing lines could be simply to lower the number of normal cytokinin producers. For example, U.S. Patent Application Publication No. 20030211082 describes an experiment conducted on wild-type barley, *Arabidopsis* and soybean (*Glycine max*) that shows that the reduction of normal cytokinin producers induces male sterility. In the experiment described in U.S. Patent Application Publication No. 20030211082 tissue was harvested from some of the soybean plants in the study and assayed for trans-Zeatin riboside as described therein. Heat treatment consists of 48 hours in a dry oven at 50° C. This treatment was shown earlier to reduce PPFM populations on seed, as described in for example, Holland, M. A & Polacco, J. C. (1992) *Plant Physiol*. 98, 942-948, which is incorporated herein by reference in its entirety. Reinoculation of heat-treated seed with wild type PPFM restored near-normal cytokinin levels. Observations of pollen development in treated plants indicate some abnormalities like germination of the pollen grains before anthesis. Thus, removing PPFMs using the phage of the invention in accordance with the methods of the invention will also lead to sterility.

In a fifth aspect of the invention, methods for treating a disease associated with elevated or above normal levels of HBB in a patient are provided. The method of the invention comprises the step of administering to a patient in need of treatment, a therapeutically effective amount of a bacteriophage which is lytic for HBB. In a preferred embodiment, the bacteriophage is selected from ATCC# PTA-5075. In yet another preferred embodiment, the method of the invention further comprises administering an antibiotic to the patient.

In an alternative embodiment, the invention provides a method of treating disease associated with elevated levels of HBB, in a patient in need thereof, comprising the steps of: a) collecting plasma from a patient to be treated; b) contacting the patient's plasma with an effective amount of a bacteriophage which is lytic for HBB for a time sufficient to reduce the HBB present in the plasma to a desired level; c) removing the dead bacterial matter from the treated plasma; and d) returning the treated plasma to the patient. The step of collecting the plasma may further comprise separating the plasma from the cellular components contained in the blood. The step of returning the treated plasma to the patient may further comprise recombining the plasma with cellular components prior to returning the treated plasma to the patient.

In one embodiment the disease to be treated is an autoimmune disease including but not limited to, multiple sclerosis, chronic fatigue syndrome, lupus erythematosis, rheumatoid arthritis and fibromyalgia. In one preferred embodiment, the disease to be treated is multiple sclerosis. As described in U.S. Pat. No. 6,255,467, elevated levels of HBB indicate the presence or likelihood of developing certain autoimmune diseases such as multiple sclerosis, chronic fatigue syndrome, lupus erythematosis, rheumatoid arthritis and fibromyalgia. Further, there is a 100% correlation between a decrease in the presence of HBB in the blood and a diminishing or complete elimination of symptoms of these diseases. In accordance with the methods of the invention, bacteriophage lytic for HBB may be used to lower levels of HBB in a patient or if desired eradicate HBB from the patient in order to reduce or eliminate symptoms of autoimmune disease.

In another embodiment, the disease to be treated is an opportunisitic infection by HBB, *Methylobacterium*, or both in a susceptible patient. Immunocompromised patients such AIDS patients and patients on immunosuppressant drugs are particularly susceptible to opportunistic infections and may be treated with the methods of the invention.

Figure 2:
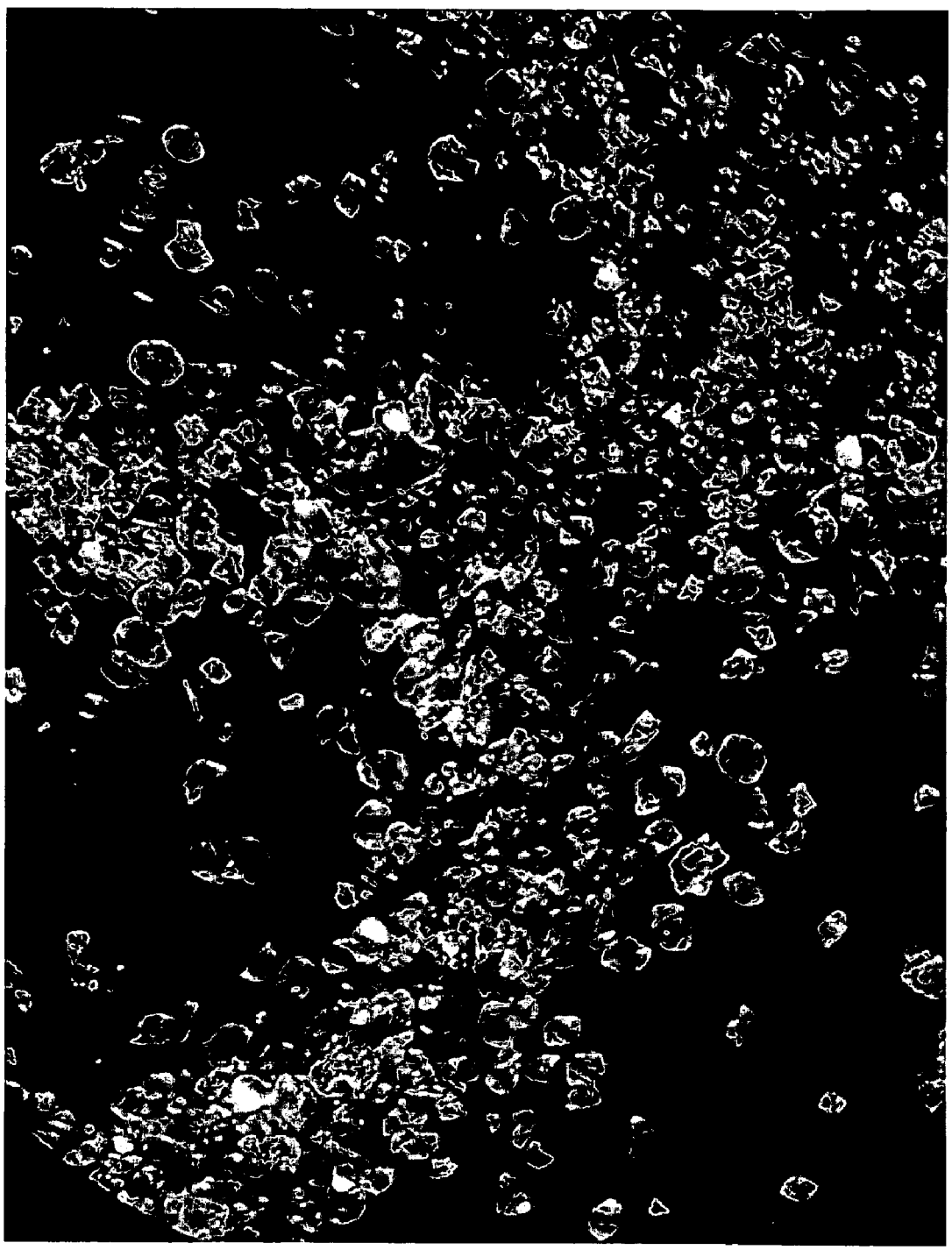
FIG. 2 is a micrograph of oxylate crystals precipitated by HBB cultures.

In another embodiment, the disease to be treated is a tissue calcification disease such as a "stone" disease including but not limited to kidney stone disease and urinary tract disease. The present inventors have observed cultures of HBB and the precipitation of crystals in the culture medium (FIG. 2). This observation was also noted in the Lindner patent cited above, and the crystals were identified as calcium oxylate. This compound is one of the materials that accumulates in stone disorders of humans, suggesting that HBB may play a role in production of mineral deposits characteristic of "stone" pathologies.

Urinary stone disease, urolithiasis, affects about 2 to 3% of the general population in the United States and other industrialized countries. In some population groups the occurrence can be significantly higher. For example, the prevalence of urolithiasis among adults in Taiwan reaches 8 to 9%, and urinary stones were reported to be the third most common disease in northern Italy. The incidence of urinary stones further increases with age, in part, due to age-related conditions such as arterial hypertension. The likelihood that a Caucasian male will develop stone disease by age 70 is about 1 in 8. While extracorporeal shock wave lithotripsy has simplified urinary stone removal, the recurrence rates remain high, reaching 50% to 70% in 10 years. Since a majority of urinary stones (75-80%) are made of calcium oxalate, the control of concentrations of calcium and/or oxalate in urine is an important part of a medical treatment program to prevent stone formation or recurrence.

Hypercalciuria is more common in patients with recurrent calcium oxalate renal stones; it is found in 50% of the cases, compared to about 35% for mild hyperoxaluria. The lowering of urinary oxalate level in accordance with the methods of the invention has a number of advantages. The contribution of oxalate to calcium oxalate saturation is considerably greater than that of calcium. As a result, a relatively small decrease in oxalate concentration could lower the calcium oxalate level below saturation, and thus prevent stone formation. Attempting to change the calcium concentration in urine as opposed to the oxalate concentration is more difficult, and risks increased oxalate absorption; it may also affect important physiological processes, such as bone calcification.

In yet another embodiment, the therapeutic methods of the invention further comprises a co-therapeutic treatment regimen comprising administering a therapeutically effective amount of an antibiotic in combination with a therapeutically effective amount of the bacteriophage of the invention to treat disease in a patient. As used herein a "co-therapeutic treatment regimen" means a treatment regimen wherein two drugs are administered simultaneously, in either separate or combined formulations, or sequentially at different times separated by minutes, hours or days, but in some way act together to provide the desired therapeutic response. Any known antibiotic suitable for the treating the particular disease and the particular patient may be used in accordance with the invention. Such suitable antibiotics include but are not limited to one or more antibiotics selected from the group consisting of beta-lactam antibiotics, aminoglycoside antibiotics, tetracyclines, and pharmaceutically acceptable salts thereof, and mixtures thereof. Suitable beta-lactam antibiotics for use in the present invention include, but are not limited to, penicillin, phenethicillin, ampicillin, azlocillin, bacmpicillin, carbenicillin, cyldlacillin, meziocillin, piperacillin, epicillin, hetacillin, cloxacillin, dicloxacillin, methicillin, nafcillin, oxacillin, and pharmaceutically acceptable salts thereof. Suitable aminoglycoside antibiotics for use in the present invention include, but are not limited to, streptomycin, kanamycin, gentamycin, amikacin, neomycin, pardomycin, tobramycin, viomycin, and pharmaceutically acceptable salts thereof. Suitable tetracyclines include tetracycline, chlortetracycline, demeclocycline, doxycycline, methacycline, oxytatracycline, rolitetracycline, minocycline, sancycline, and pharmaceutically acceptable salts thereof.

In accordance with the therapeutic methods of the inventions, therapeutically effective amounts of bacteriophage of the invention may be administered by parenteral (subcutaneously, intramuscularly, intravenously, intraperitoneally, intrapleurally, intravesicularly or intrathecally), topical, oral, rectal, inhalation, ocular, otic, or nasal route, as necessitated by choice of drug and disease. In one preferred embodiment, bacteriophages of the invention are injected directly into. the blood stream to eliminate or reduce to normal and/or desired amounts of HBB present in the blood stream.

In a sixth aspect, the invention provides pharmaceutical compositions suitable for use in the therapeutic methods of the invention. Bacteriophage of the invention are preferably formulated in pharmaceutical compositions containing the bacteriophage and a pharmaceutically acceptable carrier, and can be stored as a concentrated aqueous solution or lyophilized powder preparation. Bacteriophage may be formulated for oral administration by resuspending purified phage preparation in aqueous medium, such as deionized water, mineral water, 5% sucrose solution, glycerol, dextran, polyethylene glycol, sorbitol, or such other formulations that maintain phage viability, and are non-toxic to humans. Those skilled in the art are capable of preparing the phage preparations of the present invention in the form of a lipophilic microcapsule, a dendrimer, a liposome or other suitable form using conventional techniques known in the art which enable transfer of phages through the stomach with minimal reduction of phage viability to allow phages to reach the targeted areas of the body.

In another preferred embodiment, bacteriophage of the invention are formulated for injection. A typical composition for such purpose comprises a pharmaceutically acceptable carrier. For instance, the composition may contain about 10 mg of human serum albumin and from about 20 to 200 micrograms of the phage preparation per milliliter of phosphate buffer containing NaCl. Other pharmaceutically acceptable carriers include aqueous solutions, non-toxic excipients, including salts, preservatives, buffers and the like, as described in *Remington's Pharmaceutical Sciences,* 15th Ed. Easton: Mack Publishing Co. pp 1405-1412 and 1461-1487 (1975) and *The National Formulary XIV.,* 14th Ed. Washington: American Pharmaceutical Association (1975), the contents of which are hereby incorporated by reference. Examples of non-aqueous solvents include propylene glycol, polyethylene glycol, vegetable oil and injectable organic esters such as ethyloleate. Aqueous carriers can include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the bacteriophage compositions of the invention can be adjusted according to routine skill in the art. See, Goodman and Gilman's, *The Pharmacological Basis for Therapeutics* ($7^{th}$ ed.). The pharmaceutical compositions of the invention may contain other components so long as the other components do not reduce the effectiveness (by reducing the amount or viability) of the bacteriophage so much that the therapy is negated.

The compositions of the present invention-for animal applications preferably are administered in an amount and for a period of time effective to reduce native populations of HBB to levels considered normal for the animal species. This entails either (i) killing or obliterating sufficient bacterial microorganisms to render the microorganisms ineffective at producing abnormal or disease symptoms in the host, or (ii) reducing a sufficient quantity of bacterial microorganisms so as the render the microorganisms more susceptible to treatment using conventional antibiotics. Determining an effective amount of host-specific, non-toxic purified phage preparation to be administered in accordance with the present invention entails standard evaluations, for example, analysis of blood or body fluid levels of HBB, or HBB levels in relevant tissues, or monitoring the disease state in the patient. An assessment in this regard would generate data concerning bioavailability, absorption, metabolism, serum and tissue levels and excretion, as well as microorganism levels, markers, and cultures. The appropriate dosage and duration of treatment can be ascertained by those skilled in the art using known techniques.

In some embodiments, the pharmaceutical composition comprises bacteriophage at a titer of approximately $10^2$-$10^{11}$ PFU/ml or PFU/g. In other embodiments, the titer may be $10^7$-$10^{11}$ PFU/ml or PFU/g. In yet other embodiments, the titer may be $10^5$-$10^9$ PFU/ml or PFU/g. As will be apparent to one knowledgeable of the art, the titer used may vary according to, for example, the animal or individual being treated, the degree of infection and the state of disease progression.

In a seventh aspect of the invention, a formulation comprising a disinfecting amount of bacteriophage of the invention and a suitable carrier, diluent or dispersant can be used for the removal of HBB, *Methylobacterium*, or both, from environmental surfaces including but not limited to surfaces found in hospital settings, home and public areas, food and agriculture settings (including plants and seeds of plants), military settings and industrial settings. As used herein "a disinfecting amount" is the amount of bacteriophage sufficient to substantially reduce or eliminate the presence of HBB or a *Methylobacterium* species on an environmental surface including a plant or seeds of a plant. The term "disinfecting amount" also includes that amount of bacteriophage sufficient to prevent, inhibit, or stop the growth of *Methylobacterium* or HBB on a susceptible environmental surface or a plant or seeds of a plant. The bacteriophage may be poured, brushed, wiped painted or coated on the surface. The bacteriophage may be transferred from a transfer vehicle, which may be a towel, sponge, wipe, roller, paper product, towellete or other known transfer vehicle. The phage may be dispensed from conventional devices, including pump sprayers, aerosol containers, squirt bottles, pre-moistened towellettes. The phage may be applied directly to (e.g. sprayed onto) the area to be sanitized, or it may be transferred to the area by a towel sponge or wipe. The phage for instance could be incorporated into a wipe also containing a thickening agent. The thickening agent may be, for example, hydroxyethyl cellulose, methyl cellulose, polyvinyl pyrrolidone or mixtures of these agents, each in the concentration range 0.1 to 1% w/v. Hydroxyethyl cellulose at 0.35% w/v is the preferred component according to the instant invention. The liquid-carrying capacity of the wipe may be increased when a thickener is a component of the wipe formulation. The pH of the formulations could if desired be adjusted to the range from 5.5 to 7.5. It is believed that the best papers are hydroentangled cellulose See for instance U.S. Pat. No. 5,762,948, the disclosure of which is herein incorporated by reference.

In some embodiments, the phage formulation may be maintained under controlled conditions in order to maintain the activity level of the phage, such as in an aqueous or a non-aqueous solution, a gel, etc. In another embodiment, the phage may be stored in a freeze-dried state, and may be mixed with a liquid vehicle shortly before use. Suitable vehicles include water, chloroform, and mixtures thereof. Additional carriers, diluents or dispersants include water containing biologically compatible solutes such as salts and buffering agents as are commonly known in the art. Such salts and buffering agents may also consist of volatile solutes, such as ammonium chloride, or may be non-volatile, such as sodium chloride. This embodiment is expressly intended to include all combinations and mixtures of aqueous and organic solvents and solutes that maintain adequate phage viability, which may be greater than 50% of the original titer, more preferably greater than 75% of the original titer, or most preferably greater than 95% of the original titer. In another embodiment, the phage may be maintained at a controlled temperature. In another embodiment, the phage may be maintained at a controlled pressure.

In an eighth aspect, the invention provides a kit for applying the bacteriophage of the invention to a surface or a plant, or seeds of a plant for disinfecting or removing HBB or *Methylobacterium*. The kit comprises a container for storing the bacteriophage in a suitable carrier, diluent or dispersant, and a mechanism for dispersing or dispensing the bacteriophage from the container. In general, any mechanism that provides substantially even dispersion of the phage may be used. Further the phage should be dispersed or dispensed from the container in a manner that does not cause damage to the surface on which the phage is being applied and also does not damage the phage itself. One suitable mechanism is a spray mechanism that is directly associated with the container. In this device, the pressure is generated by the user when the user depresses the pump (or, if a trigger pump, when the user pulls the "trigger"), causing the phage and its carrier to be forced through the nozzle of the mechanism. In another embodiment, the container is a canister in which the phage are stored under pressure are dispersed via a spray mechanism in a conventional manner by depressing a button, or a valve, on top of the canister. In another embodiment, a fogger or misting mechanism directly associated with the container may be used to disperse the phage over an area. In another embodiment, the mechanism may be a roller or brush such as a paint roller or paint brush. In another embodiment, the mechanism for dispersion is cloth wipe, a paper wipe, a towel, a towelette, or a sponge, that may be prepackaged with the phage or phage formulation similar to an alcohol wipe.

In another embodiment, the kit may further comprise a second container containing a suitable carrier, diluent or dispersant. As discussed above, the phage may be stored in its freeze-dried form in a suitable container, and then combined with the carrier, diluent or dispersant shortly before use. When a user wishes to use the phage, the user combines the phage in a first container with the carrier, diluent or dispersant from the second container prior to applying the formulation to a surface to be disinfected. Other technologies for storing the phage and solvent separately, and causing their mixture shortly before use, are well-known, and may also be used.

The present invention now will be illustrated by the following experiments and examples which are intended to further exemplify particularly preferred embodiments of the invention, and are not meant to limit the invention.

EXAMPLES

Example 1

Phages were isolated from water, soil, and plant material in the greenhouse attached to Devilbiss Hall on the SU campus as follows: Water samples (with associated soil, plant material etc) from a floor drain, from around the base of flower pots, from the muck on the greenhouse benches, etc, were collected and returned to the lab. In the lab, 50 mL cultures of PPFM bacteria (soybean isolate, SL1, ATCC 202211) were inoculated with 1 mL aliquots of the greenhouse samples and incubated for 5 days on a shaker (225 rpm) at room temperature. This constituted an enrichment step, since it was expected that phages if present in the greenhouse samples, would be at very low titer. Following the enrichment, the cultures were centrifuged (7000 rpm, 10 minutes in a clinical, swinging bucket centrifuge) to remove whole cells and debris. Supernatants were then filtered through a 0.2 μm filter. Such a filter will allow bacteriophages to pass through, but will retain bacterial cells and cellular debris. The resulting phage suspensions were then streaked on lawns of *Methylobacterium* isolates to test their ability to lyse the bacteria. As shown in FIG. 1, the phage induced cell lysis on the bacterial lawn.

Example 2

Medium AM1, routinely used for the culture of *Methylobacterium* was modified by the addition of lactalbumin hydrolysate (2.6 g per liter), yeast extract (2 g per liter), and lactose (4 g per liter). These additions are suggested by the method of Lindner et al in U.S. Pat. No. 6,255,467. The medium was sterilized by autoclaving before use.

Flasks of 125 mL of the above medium were inoculated with whole human blood of the primary inventor (4 drops per flask, harvested from the fingertip) in a sterile containment hood. The flasks were incubated at room temperature on a gyrotary shaker (235 rpm).

After 4 days, the inoculated flasks began to show signs of bacterial growth. Small samples of the inoculated medium were withdrawn and examined microscopically. The bacteria matched in size and shape the description and micrographs made by Lindner in the above referenced patent. Growth characteristics of the cultures are very similar to those of other *Methylobacterium* cultures we have grown in the lab. Interestingly, the putative Human Blood Bacterium (HBB) cells are morphologically distinct from other *Methylobacterium* cells we have looked at. In morphology, the rapidly dividing cells assume a coccoid shape which, as growth of the culture slows, becomes more rod-like. The bacteria isolated from blood do not grow in unsupplemented AM1 medium. Twenty-one 4 mL aliquots of the culture of blood bacteria were placed in sterile 15 mL capped tubes and each was infected with 200 uL of a phage lysate prepared from a different one of our phage isolates. Four tubes were similarly prepared, but remained uninfected for comparison.

After 24 hours, the infected tubes showed clearing and accumulation of bacterial debris, signs of bacterial lysis.

Example 3

Example 2 was repeated substituting the human blood bacterium, HBB, for each of the following *Methylobacterium* species:
Methylobacterium mesophilicum;
Methylobacterium radiotolerans;
Methylobacterium extorquens;
Lab isolate SL1 (ATCC 202211);
2 lab isolates from Barley;
2 lab isolates from Celosia;
2 lab isolates from broccoli; and
2 lab isolates from soy seed coat.

In each of the above tests, either an aqueous dilution of phages was used to infect a liquid culture of the PPFM and the culture observed for lysis as in Example 2 or phage dilutions were spotted onto the surface of a PPFM lawn and observed for the appearance of cleared zones of lysis in the bacteria as shown in FIG. 1. (lawn=several mLs of a PPFM culture poured on to the surface of a Petri dish of solidified PPFM medium and allowed to grow until covering the surface of the dish). In each of the above experiments, lysis of the bacteria by the bacteriophages was observed.

Example 4

Figure 3A:
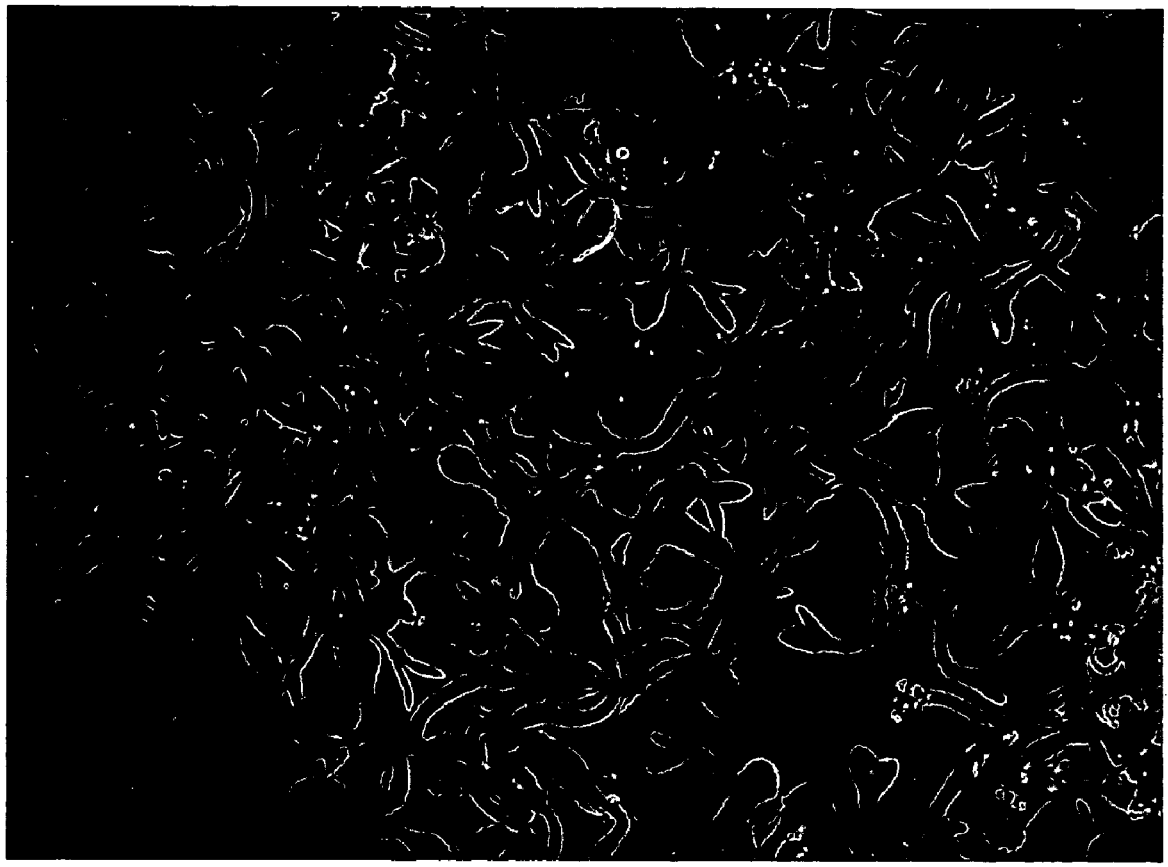
FIG. 3a is a micrograph showing the germination of plant seeds with no phage present.
Figure 3B:
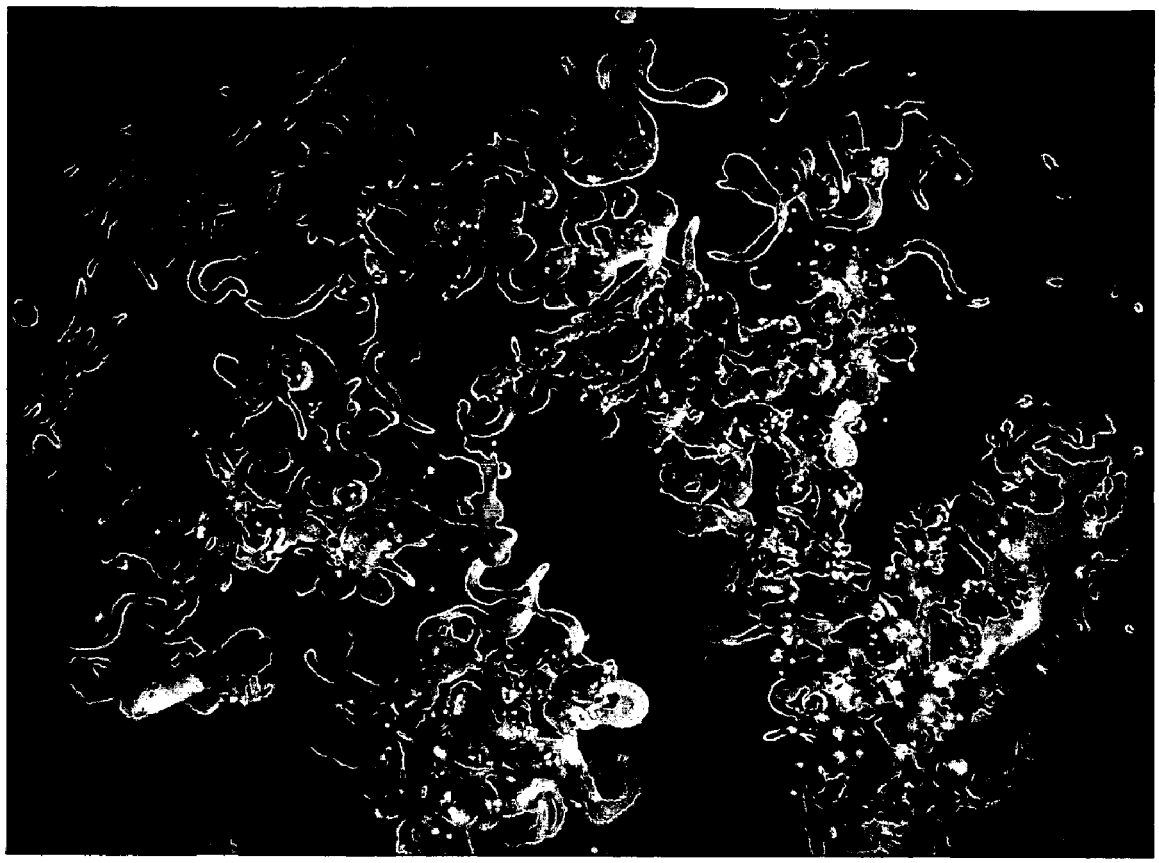
FIG. 3b is a micrograph showing that the germination of plant seeds with phage present.

Referring to FIGS. 3a and 3b, FIG. 3a shows *Arabidopsis* seeds germinated in phage dilution medium (no phage present). FIG. 3b shows seeds germinated in the presence of the bacteriophage of the invention. Note the reduced rate of germination in FIG. 3b. Seeds treated with phage can be restored to germinability by washing and the addition of PPFM bacteria.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. The bacteriophage deposited as ATCC #PTA-5075.

2. A method for purifying a bacteriophage which is lytic for *Methylobacterium* species comprising the steps of:
 a) obtaining bacteriophage from a sample that has been in contact with plant matter;
 b) plating the bacteriophage onto a medium comprising at least one *Methylobacterium* species derived from a plant or seeds of a plant;
 c) collecting plaques formed in the *Methylobacterium*-containing medium; and
 d) purifying the isolated plaques.

3. The method of claim 2 wherein steps b-d are repeated with the product of step (d) until a virulent bacteriophage preparation is obtained.

4. The method of claim 2 wherein the *Methylobacterium* species is a Pink Pigmented Facultative Methylotrophs (PPFM).

5. The method of claim 2 wherein the PPFM is selected from the group consisting of *M. mesophilicum, M. organophilum* and *M. extorquens* and combinations thereof.

* * * * *

UNITED STATES PATENT AND TRADEMARK OFFICE
CERTIFICATE OF CORRECTION

| | | |
|---|---|---|
| PATENT NO. | : 7,550,283 B2 | Page 1 of 1 |
| APPLICATION NO. | : 10/821640 | |
| DATED | : June 23, 2009 | |
| INVENTOR(S) | : Holland et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 630 days Delete the phrase "by 630 days" and insert -- by 1067 days --

Signed and Sealed this

Seventeenth Day of August, 2010

David J. Kappos
*Director of the United States Patent and Trademark Office*